(12) United States Patent
Sale et al.

(10) Patent No.: US 8,782,841 B2
(45) Date of Patent: Jul. 22, 2014

(54) BRUSHHEAD/HANDLE INTERFACE FOR A POWER TOOTHBRUSH

(75) Inventors: Kyle Sale, Snoqualmie, WA (US); Patrick A. Headstrom, Seattle, WA (US); Tyler G. Kloster, Snoqualmie, WA (US)

(73) Assignee: Koninklijke Philips N.V., Eindhoven (NL)

(*) Notice: Subject to any disclaimer, the term of this patent is extended or adjusted under 35 U.S.C. 154(b) by 437 days.

(21) Appl. No.: 12/374,871

(22) PCT Filed: Dec. 9, 2008

(86) PCT No.: PCT/IB2008/055168
§ 371 (c)(1),
(2), (4) Date: Jun. 25, 2010

(87) PCT Pub. No.: WO2009/077922
PCT Pub. Date: Jun. 25, 2009

(65) Prior Publication Data
US 2010/0251493 A1  Oct. 7, 2010

Related U.S. Application Data

(60) Provisional application No. 61/014,496, filed on Dec. 18, 2007.

(51) Int. Cl.
*A46B 13/02* (2006.01)
*A61C 17/34* (2006.01)

(52) U.S. Cl.
USPC .......................................... 15/22.1; 15/22.2

(58) Field of Classification Search
USPC ................................. 15/22.1, 22.2
See application file for complete search history.

(56) References Cited

U.S. PATENT DOCUMENTS

| | | | |
|---|---|---|---|
| 3,369,265 A | | 2/1968 | Halberstadt et al. |
| 3,851,984 A | * | 12/1974 | Crippa ........................ 403/322.4 |
| 5,412,827 A | * | 5/1995 | Muller et al. .................. 15/22.1 |
| 5,697,117 A | | 12/1997 | Craft |
| 5,842,245 A | | 12/1998 | Pai |
| 6,588,042 B2 | * | 7/2003 | Fritsch et al. .................. 15/22.1 |
| 6,836,917 B2 | | 1/2005 | Blaustein et al. |
| 7,222,381 B2 | | 5/2007 | Kraemer |
| 2004/0010872 A1 | | 1/2004 | Chiang |
| 2005/0100867 A1 | | 5/2005 | Hilscher et al. |

FOREIGN PATENT DOCUMENTS

| | | |
|---|---|---|
| JP | 04040905 A | 2/1992 |
| WO | 0076420 A1 | 12/2000 |
| WO | 2005046506 A1 | 5/2005 |

* cited by examiner

*Primary Examiner* — Randall Chin

(57) ABSTRACT

The brushhead/handle interface includes a brushhead assembly (20) which has a brush member (26) for cleaning teeth. A driveshaft (14) extends from a handle portion (12) of the toothbrush (10), which is driven in an oscillating manner through a selected rotational angle. The driveshaft includes one or more contact regions (49). The coupling member includes an interface portion or portions (46) which are forced against the contact regions of the driveshaft by a single spring member when the driveshaft is inserted into the coupling member. The single spring (34) exerts a sufficient force on the interface portions of the coupling member against the contact regions of the driveshaft to produce both a reliable torque transfer between the driveshaft and the brushhead assembly and to maintain axial retention of the brushhead assembly on the driveshaft during operation of the toothbrush.

19 Claims, 9 Drawing Sheets

BRUSHHEAD/HANDLE INTERFACE FOR A POWER TOOTHBRUSH

This invention relates generally to handle/brushhead interface arrangements for power toothbrushes, and more specifically concerns such an interface in which the torque transfer function and axial retention function of the brushhead relative to the toothbrush driveshaft is accomplished by a single spring and coupling combination.

Many power toothbrushes have a structural arrangement in which a driveshaft, driven rotationally or through a selected angle of oscillation, extends from a handle portion of the toothbrush, with the drive mechanism being contained within the handle portion. A removable brushhead assembly fits onto the extending driveshaft. The brushhead assembly includes a coupling member, which fits into an arm portion of the brushhead assembly. At the distal end of the arm portion is a brush member for cleaning teeth. The driveshaft extends into and securely mates with the coupling member.

The structural interaction between the drive shaft and the coupling member must be such as to reliably transfer the torque of the moving driveshaft to the brushhead and to maintain the torque transfer under load. The load refers to a combination of the torque created by the inertial mass of the oscillating brushhead and the forces created by the interaction with the tissues and other elements of the user's mouth. The structural interaction must also be sufficient to hold the brushhead on the driveshaft, which is referred to as axial retention, during operation of the toothbrush, while also permitting the brushhead to be conveniently removed by the user. Axial retention can be a challenging aspect of such an arrangement if the brushhead is to be removed regularly for cleaning or other purposes. The arrangement must be such that the functions of torque transfer and axial retention are not degraded even after the brushhead assembly has been removed numerous, perhaps hundreds, of times during the lifetime of the brushhead assembly.

The present arrangement is capable of reliably providing both the torque transfer and the axial retention functions, while permitting a large number of removals of the brushhead assembly from the driveshaft.

The disclosed arrangement is a brushhead/handle interface for a power toothbrush, comprising: a brushhead assembly having a brush member at one end thereof for cleaning teeth; a driveshaft extending from a handle portion of the toothbrush, driven such that it oscillates through a selected rotational angle, the driveshaft having one or more contact regions in which are located interface surfaces; a coupling member positioned at the other end of the brushhead assembly for receiving the driveshaft, wherein the coupling member includes one or more interface portions which come into physical contact with said interface surfaces of the driveshaft when the driveshaft is inserted into the coupling member; and a spring member positioned so as to exert a force against the coupling member large enough that the physical contact between said interface portion or portions of the coupling member and said one or more contact regions of the driveshaft is sufficient to produce a reliable torque transfer between the driveshaft and the brushhead assembly and to maintain axial retention of the brushhead assembly on the driveshaft during operation of the toothbrush, while permitting a user to remove the brushhead assembly from the driveshaft when the toothbrush is not operating.

Figure 1:
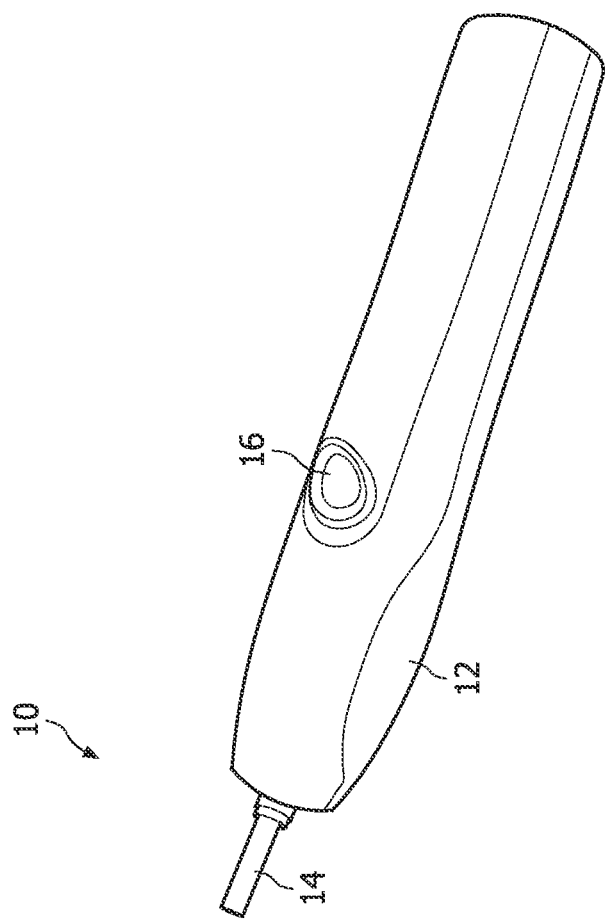
FIG. 1 is a partially exploded view of a toothbrush described herein comprising a handle portion and a brushhead assembly portion.
Figure 1:
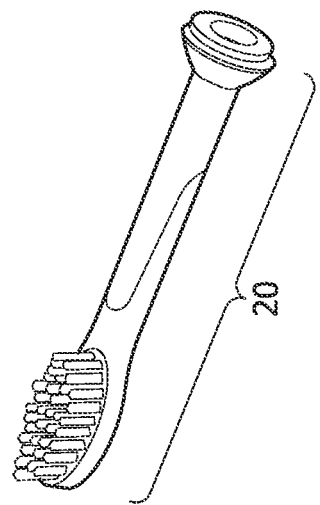

FIG. 1 shows a toothbrush 10 which includes a handle portion 12 with a drive assembly which includes an extending driveshaft 14, the driveshaft driven by a motor (not shown) positioned within handle 12. The motor moves the driveshaft in an oscillating manner through a selected angle. The motor is controlled by a user-operated on/off switch 16. Removably mounted on driveshaft 14 is a brushhead assembly 20.

Figure 2:
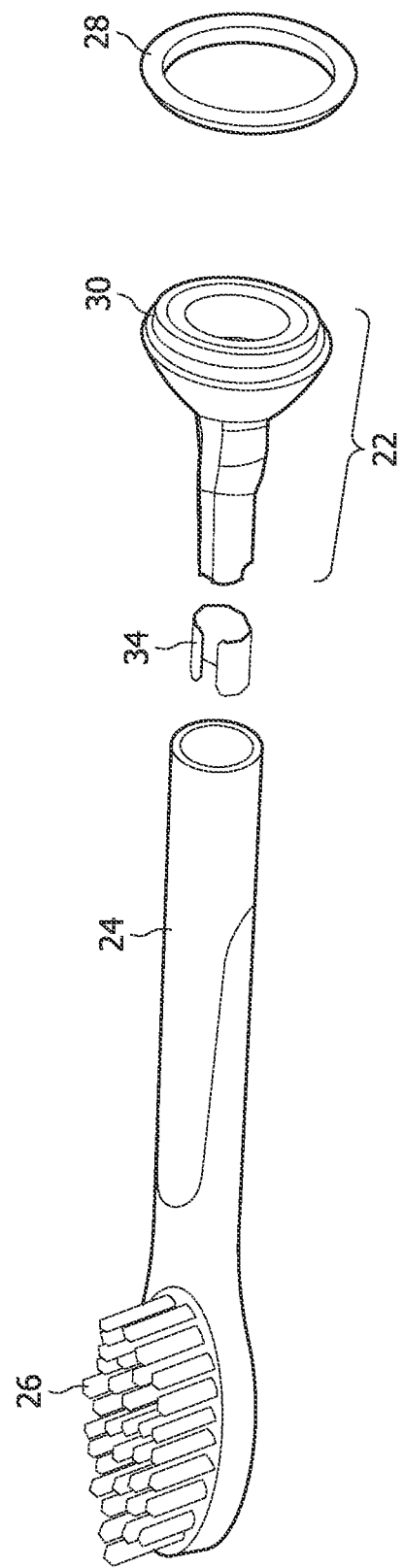
FIG. 2 is an exploded view of the brushhead assembly portion of FIG. 1.

Referring to FIG. 2, the brushhead assembly 20 includes a coupling assembly 22 which fits snugly into and is captured by an arm portion 24 of the brushhead assembly. Positioned on a distal end of the arm portion is a conventional brush member 26 which cleans the teeth. In operation, brush member 26 rotates/oscillates back and forth through a selected angle to accomplish the desired cleansing. The coupling assembly may further include a ring 28 at the proximal end 30 of the coupling assembly. The ring can be different colors to identify the user of the brushhead assembly. The coupling assembly further includes a spring member 34 which fits around a portion of the body of the coupling assembly 22.

Figure 3A:
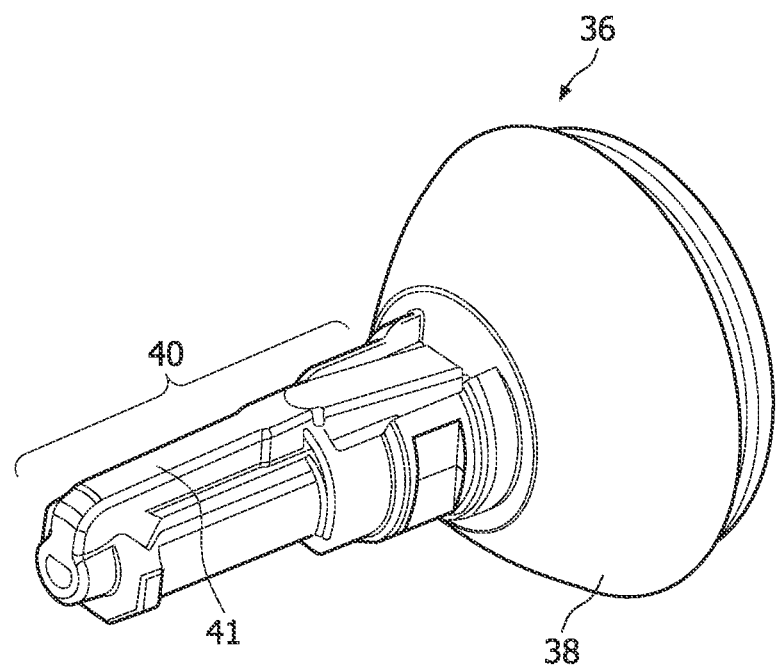
FIGS. 3A and 3B are isometric views of the coupling member shown in FIG. 2.
Figure 3B:
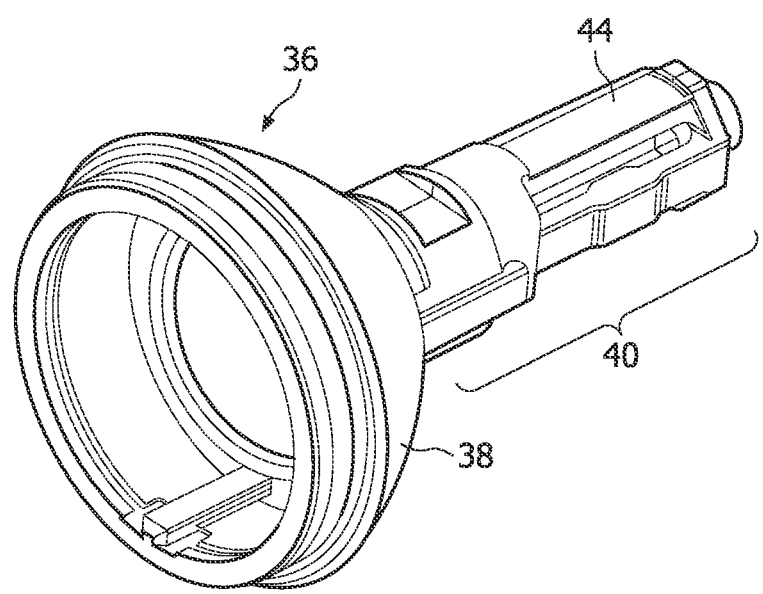

The coupling assembly is shown in more detail in FIGS. 3A and 3B. It includes a base portion 36, the lower end of which may be configured to receive ring 28. Forward of ring 28 is an inwardly angled surface portion 38, substantially cone-shaped. Forwardly of the angled portion 38 is a coupling body portion 40. The body portion 40 includes an internal axial opening which receives the driveshaft 14. Along one side of the body portion 40 is a rib 41 which extends for substantially the length of the body portion, the rib fitting snugly into a mating slot in arm portion 24. The rib 41 locates and maintains the physical relationship between the coupling assembly and the arm portion 24.

On the opposite side of the body portion from rib 41 is a coupling strip 44. This is shown in both FIG. 3B and FIG. 5. In the embodiment shown, coupling strip 44 is fixedly mounted to the body portion 40 at the opposing ends of the strip and is free to flex to some extent between its two ends. The body portion 40 is made from acetal which permits flexing of the coupling strip to occur, while being tough enough to resist abrasion and compression deformation or creep during the life of the brushhead. Coupling strip 44 is approximately 0.6 mm long and approximately 0.3 mm wide.

It is approximately 0.80 mm thick, except for a first interface contact member portion 46, which is approximately 1.323 mm thick. The first interface contact member 46 is a bulge or block which extends inwardly from coupling strip 44 approximately 0.16 mm, sufficient to mike a significant physical contact with the inserted driveshaft 14. Alternatively, the first interface contact member could be located on spring member 34, in which case the coupling strip 44 could be eliminated.

Figure 4:
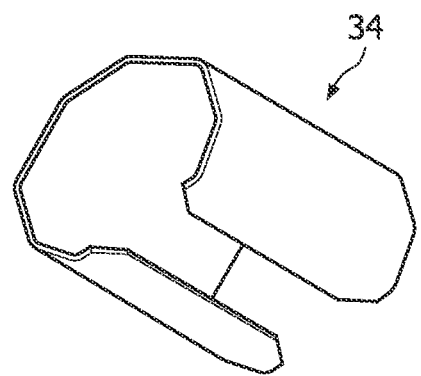
FIG. 4 is an isometric view of a spring member portion of the brushhead assembly of FIG. 2.

As indicated above, spring member 34 is positioned around a part of the body portion 40 of the coupling assembly. Spring member 34 is shown in more detail in FIG. 4. The spring member is, in the embodiment shown, an angled C-shaped configuration, although it could be other configurations, including an oval or a closed arrangement. The spring could also be a leaf spring or a coil spring. Spring member 34 is arranged and configured to provide an inwardly directed force against the body portion of the coupling assembly with sufficient frictional and physical contact between the body portion and the driveshaft to produce the desired torque transfer as well as axial retention. In the embodiment shown, this force is in the range of 30-60 newtons, preferably approximately 50 newtons. The body portion of the coupling assembly and the extending portion of the driveshaft can be of various configurations to achieve this desired functional result.

Figure 6:
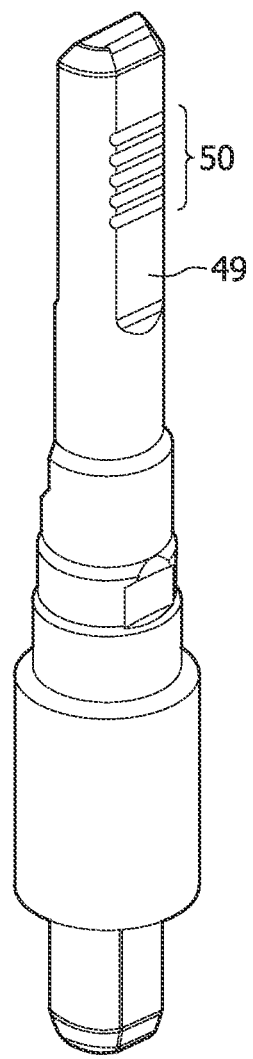
FIG. 6 is an isometric view of a driveshaft with a first contact surface embodiment.
Figure 8:
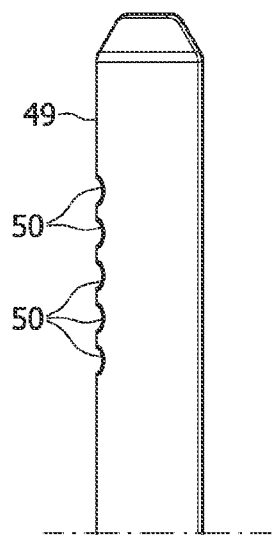
FIG. 8 is a side elevational view of the driveshaft of FIG. 6.

In one embodiment, referring to FIGS. 6 and 8, a contact portion 49 on the driveshaft includes a plurality of grooves 50 which extend laterally across the contact portion, which is flat. In this embodiment, there are a total of five grooves, which number can be varied. The grooves are approximately 0.10 mm deep, have a generally curved configuration, with a distance of 0.65 mm center to center. The physical interaction between the grooves 50 in the first contact portion of the driveshaft and the first interface contact member 46 produces a good torque transfer between the driveshaft and the brushhead assembly, as well as sufficient axial retention to maintain the brushhead assembly on the driveshaft during operation of the toothbrush. The axial retention is also such as to permit the user to conveniently remove the brushhead from the driveshaft for cleaning and the like, without degrading the torque transfer and axial retention functions.

Figure 7:
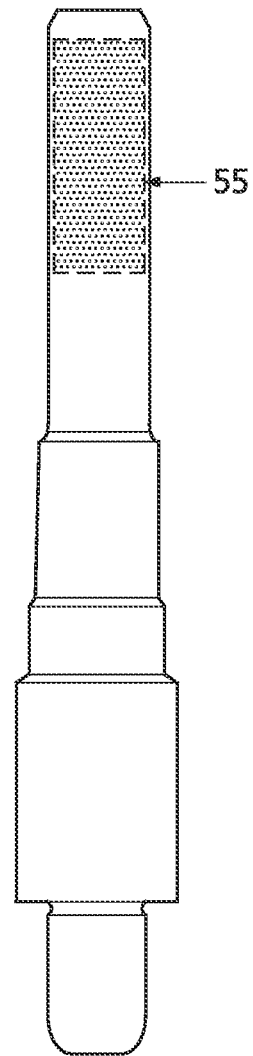
FIG. 7 is an elevational view of a driveshaft with another contact surface embodiment.

FIG. 7 shows another embodiment of a driveshaft contact portion 55. In this embodiment, contact portion 55 has been roughened, such as by sandblasting or the like. The surface finish is 0.80 μmeters or rougher, e.g. up to 1.6 μmeters. This driveshaft surface, with the interface contact member 46 of the coupling member described above, is also sufficient to accomplish the desired torque transfer and axial retention functions.

Figure 5:
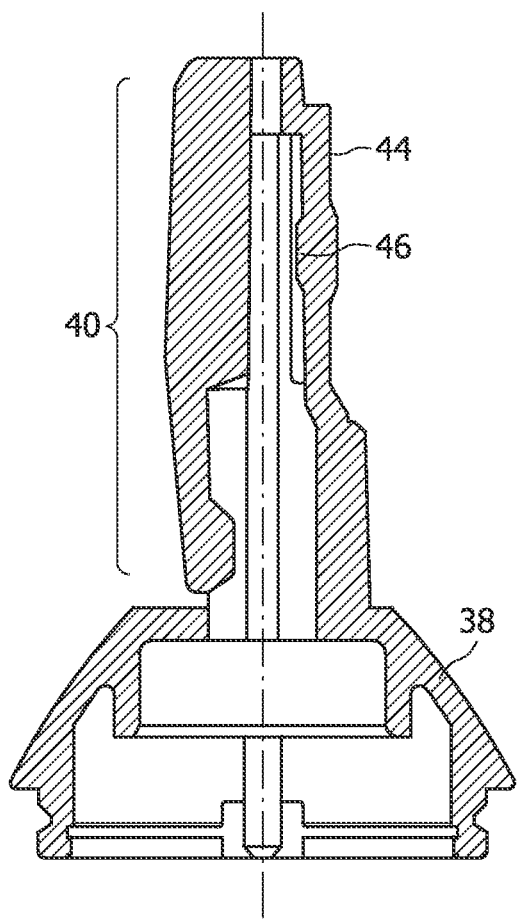
FIG. 5 is a cross-sectional view of the coupling member of FIG. 2.
Figure 9:
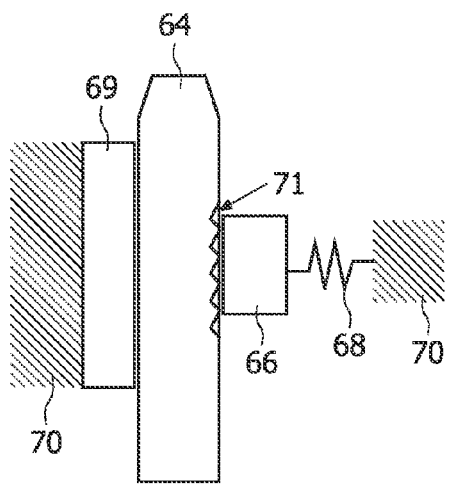
FIG. 9 is a simplified cross-sectional view of the handle/brushhead assembly interface of FIGS. 5, 6 and 8.

FIG. 9 shows a simplified representation of the embodiment of FIGS. 5, 6 and 8. It includes a grooved driveshaft 64, an interface contact member 66 of a coupling member and a representation of the spring function at 68. Portions 70-70 refer generally to the brushhead assembly arm, in which the coupling assembly is mounted. Portion 69 refers to the part of the coupling member on the opposite side of the driveshaft from the interface contact member. In this embodiment, the spring pressure is against the interface contact member, which bears directly against the grooves 71 on the driveshaft 64.

Figure 10A:
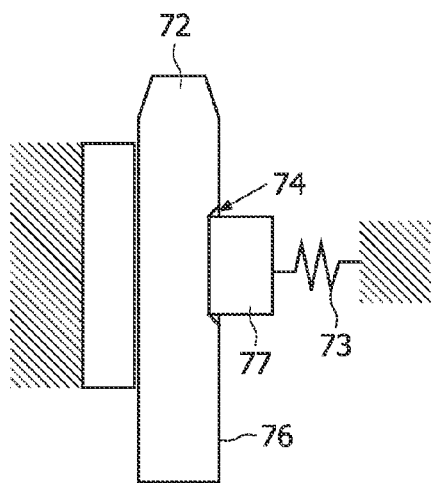
FIGS. 10A-10C are simplified cross-sectional views of three variations of another embodiment of the brushhead assembly/handle interface.
Figure 10B:
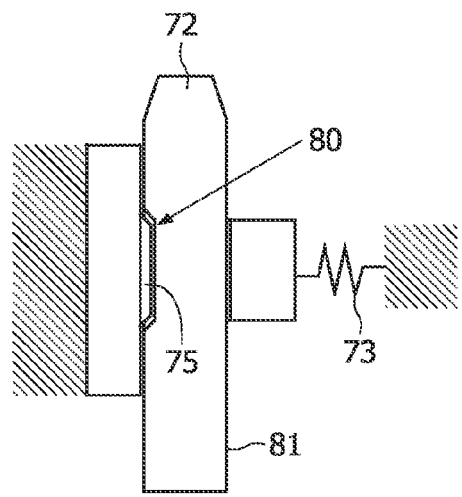
Figure 10C:
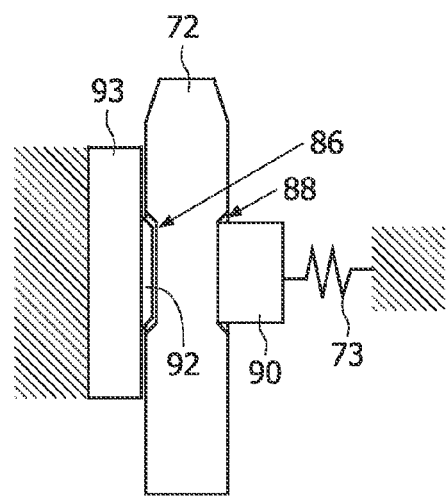

FIGS. 10A-10C show another embodiment in which driveshaft 72 has a slot in a surface thereof, the slot being sufficiently large to accommodate an interface contact member portion of the coupling assembly. Each of the embodiments of FIGS. 10A-10C includes a spring function 73. FIG. 10A shows a slot 74 in surface 76 of driveshaft 72 and an interface contact member 77 fitting therein. FIG. 10B shows a slot 80 in surface 81 of the driveshaft opposite from spring function 73 and an interface contact member 75 which extends from coupling assembly on the opposite side from spring function 73 into slot 80. FIG. 10C shows a driveshaft 72 with slots 86 and 88 on both (opposing) sides of the driveshaft, into which are fitted a first interface contact member 90 on the same side of the driveshaft as spring function 73, and a second interface contact member 92 extending from coupling assembly 93 on the opposite side of the driveshaft from spring function 73.

Figure 11:
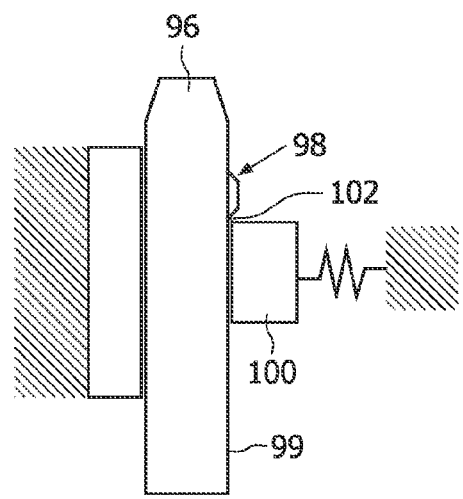
FIG. 11 is a simplified cross-sectional view of another embodiment of the brushhead assembly/handle interface.

FIG. 11 shows a further embodiment, in which a driveshaft 96 includes a protrusion 98 from surface 99 thereof, on the spring function side of the driveshaft. Interface contact member 100 is positioned adjacent to one end 102 of the driveshaft protrusion 98.

Figure 12A:
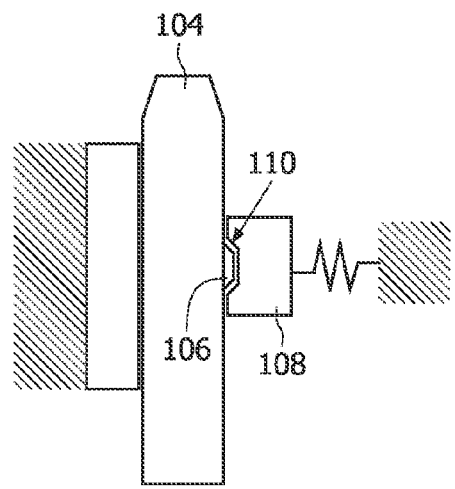
FIGS. 12A-12C are simplified cross-sectional views of three variations of another embodiment of the brushhead assembly/handle interface.
Figure 12B:
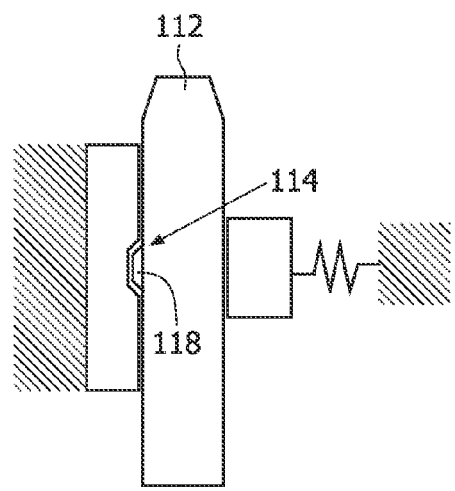
Figure 12C:
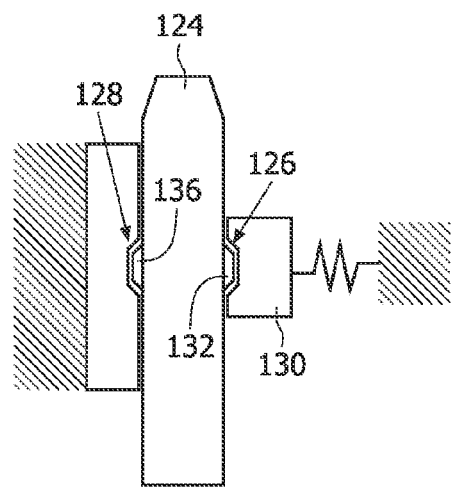

FIGS. 12A-12C show additional embodiments in which protrusions are located on one or both sides of the driveshaft, with the interface contact members having a slot into which the protrusions fit. In FIG. 12A, driveshaft 104 includes a protrusion 106 on the spring function side of the driveshaft. Interface contact member 108 includes a slot 110 into which protrusion 106 fits. FIG. 12B shows a driveshaft 112 with a protrusion 114 on the side opposite from the spring function side. Protrusion 114 fits into a slot 118 in the coupling assembly on the side opposite from the spring function side of the coupling assembly. FIG. 12C shows a driveshaft 124 having protrusions 126 and 128 on opposing sides of the driveshaft. On the spring side of the driveshaft is interface contact member 130, which has a slot 132 therein to receive protrusion 126, while in the opposing side of the coupling assembly is a slot 136 into which fits protrusion 128.

Figure 13A:
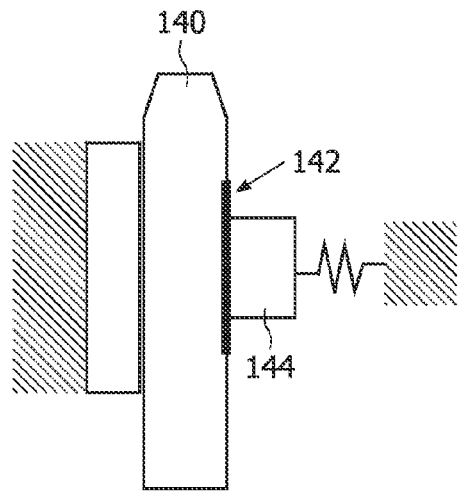
FIGS. 13A-13C are simplified cross-sectional views of three variations of a still further embodiment of the brushhead assembly/handle interface.
Figure 13B:
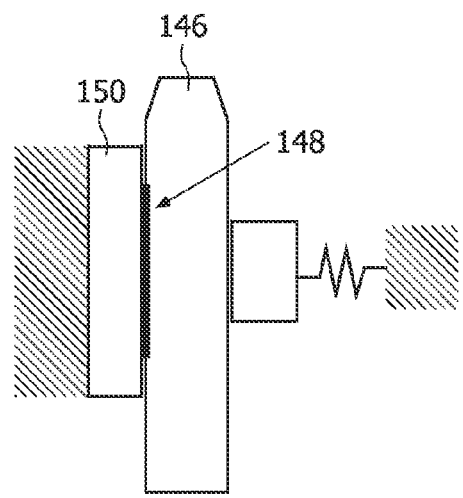
Figure 13C:
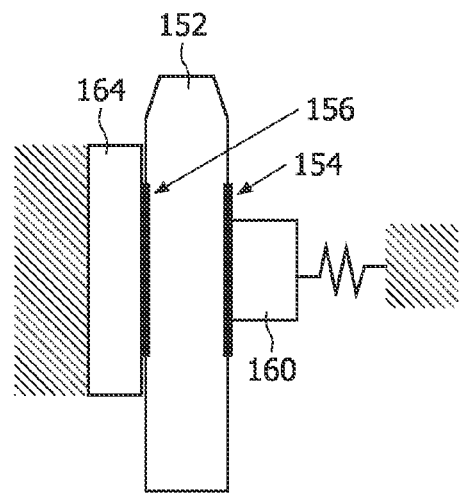

FIGS. 13A-13C show further embodiments with roughened surfaces on contact portions of the driveshaft, like that shown in FIG. 7. FIG. 13A includes a driveshaft 140 having a roughened surface region 142 on the spring function side of the driveshaft. Interface contact member 144 makes sufficient physical contact with the roughened surface 142 to accomplish the desired functions. FIG. 13B shows a driveshaft 146 with a roughened surface region 148 on the side of the driveshaft opposite from the spring function. Coupling assembly portion 150 on the opposite side of the driveshaft makes the required physical contact with the roughened region 148. FIG. 13C shows a driveshaft 152 with roughened surface regions 154 and 156 on opposite sides of the driveshaft. Interface contact member 160 engages roughened surface region 154, while the surface of coupling assembly portion 164 on the opposite side from interface member 160 engages roughened surface region 156.

It should be understood that other arrangements/configurations between the driveshaft and portions of the coupling assembly are possible.

Although a preferred embodiment of the invention has been disclosed here for the purposes of illustration, it should be understood that various changes, modifications and substitutions may be incorporated in the embodiment without departing from the spirit of the invention, which is defined by the claims which follow.

The invention claimed is:

1. A brushhead for use with a power toothbrush, comprising:
   a toothbrush member (26);
   a mounting neck (24) on which the toothbrush member is mounted;
   a coupling member (22) separate from the mounting neck, which mates a driveshaft (14) from a motor drive assembly contained within a handle assembly portion (12) of the toothbrush to the mounting neck, including an engagement member on an outer surface of the coupling member and a mating slot on an interior portion of the mounting neck; and a spring member (34) having a spring action about a longitudinal axis of the coupling member fitted on an extending portion of the coupling member, into which coupling member the driveshaft fits sufficiently tightly, with the force of the spring member, to transfer oscillating action of the driveshaft to the mounting neck, and vice versa, as the brushhead oscillates in response to action of the driveshaft, wherein the spring member contacts and extends around a portion of an exterior surface of the coupling member but does not directly contact the driveshaft.

2. The brushhead of claim 1, wherein the coupling member includes a coupling strip member (44) mounted at both ends so as to permit movement of the strip member therebetween, and wherein the coupling strip member includes an interface portion, extending inwardly in the direction of the driveshaft, resulting in physical contact between said interface portion and an interface surface of the driveshaft when the driveshaft is received in the brushhead assembly.

3. The brushhead of claim 1, wherein the user is able to remove the brushhead assembly a large plurality of times without degrading the torque transfer and axial retention capabilities.

4. The brushhead of claim 1, wherein the spring member is substantially C-shaped in cross-section.

5. The brushhead of claim 1, wherein interface surfaces of the driveshaft include a plurality of lateral grooves (50) which extend across the contact region of the driveshaft and wherein an interface portion of the coupling member is substantially larger than any of the grooves.

6. The brushhead of claim 1, wherein interface surfaces of the driveshaft include a slot (74), and wherein an interface portion (77) of the coupling member is configured to fit within the slot.

7. The brushhead of claim 1, wherein interface surfaces of the driveshaft include a slot (80) on a side of the driveshaft opposite from a side against which the spring force is exerted, and wherein one of the interface portions (75) of the coupling member includes a protrusion configured to fit within said slot.

8. The brushhead of claim 1, wherein interface surfaces of the driveshaft include slots (86, 88) in opposing sides thereof and wherein the interface portions (90, 92) of the coupling member include protrusions configured to fit within the slots.

9. The brushhead of claim 1, wherein interface surfaces of the driveshaft include a protrusion (98) and wherein an interface portion (100) of the coupling member fits against the driveshaft adjacent the protrusion.

10. The brushhead of claim 1, wherein interface surfaces of the driveshaft include at least one protrusion (106) extending therefrom, and wherein the interface portions of the coupling member include a slot (110) into which the driveshaft protrusion fits.

11. The brushhead of claim 1, wherein interface surfaces of the driveshaft include protrusions (126, 128) on opposing sides thereof, and wherein the interface portions of the coupling member include slots (132, 136) which receive the protrusions.

12. The brushhead of claim 1, wherein interface surfaces of the driveshaft include at least one roughened region (142), and wherein an interface portion (144) of the coupling member makes said physical contact with the roughened portion.

13. The brushhead of claim 1, wherein interface surfaces of the driveshaft include roughened regions (154, 156) on opposing sides of the driveshaft, and wherein the interface portions (160, 164) of the coupling member make said physical contact with the roughened regions.

14. The brushhead of claim 1, wherein the spring member is insertable onto and removable from the extending portion of the coupling member and wherein the spring member is configured and arranged structurally to produce a sufficiently tight fit between the spring member, coupling member and the driveshaft to react and/or transfer torque between the driveshaft and the brushhead when the driveshaft is operatively inserted into the coupling member and the coupling member is operatively inserted into the mounting neck.

15. The brushhead of claim 1, wherein the spring member produces a preload which is sufficient to prevent relative movement between the brushhead and the driveshaft while permitting convenient removal of the mounting neck and the toothbrush member from the driveshaft.

16. The brushhead of claim 1, wherein the spring member is an angular C shape which fits around an exterior surface of the coupling member.

17. The brushhead of claim 1, wherein the spring member is in the form of a closed oval, a closed circle, a coil spring or a leaf spring.

18. In a brushhead assembly for use with a power toothbrush which comprises a toothbrush element (26), a mounting neck (24) on which the toothbrush element is mounted and a coupling member (22) which mates a driveshaft (14) from a motor drive assembly within a handle assembly portion (12) of the toothbrush to the mounting neck, the improvement comprising:

a spring member (34), having a spring action about a longitudinal axis of the coupling member fittable onto an extending portion of the coupling member (22), into which coupling member the driveshaft fits sufficiently tightly, with the force produced by the spring action of the spring member against the coupling member, that the coupling member follows oscillating action of the driveshaft and reacts and/or transfers the torque from the resulting oscillating action of the brushhead assembly, wherein the spring member fits around a portion of an exterior surface of the coupling member and does not contact the driveshaft directly.

19. In the brushhead assembly of claim 18, the improvement further comprising the coupling member being separate from the neck member and including an longitudinally extending engaging member which fits into a mating slot of the mounting neck.

\* \* \* \* \*